United States Patent [19]
Holmes-Farley et al.

[11] Patent Number: 5,985,938
[45] Date of Patent: Nov. 16, 1999

[54] METHOD FOR REDUCING OXALATE

[75] Inventors: Stephen Randall Holmes-Farley, Arlington; W. Harry Mandeville, III, Lynnfield, both of Mass.

[73] Assignee: Geltex Pharmaceuticals, Inc., Waltham, Mass.

[21] Appl. No.: 08/964,956

[22] Filed: Nov. 5, 1997

[51] Int. Cl.$^6$ .................................................. A61K 47/00
[52] U.S. Cl. .......................................................... 514/789
[58] Field of Search ........................ 424/78.12; 514/610, 514/789

[56] References Cited

U.S. PATENT DOCUMENTS

| | | | |
|---|---|---|---|
| 4,143,130 | 3/1979 | Imondi et al. | 424/81 |
| 4,198,396 | 4/1980 | Seidel et al. | 424/81 |
| 5,244,913 | 9/1993 | Coulter et al. | 514/358 |
| 5,607,669 | 3/1997 | Mandeville, III et al. | 424/78.12 |
| 5,618,530 | 4/1997 | Mandeville, III et al. | 424/78.12 |
| 5,624,963 | 4/1997 | Mandeville, III et al. | 514/789 |
| 5,679,717 | 10/1997 | Mandeville, III et al. | 514/742 |
| 5,693,675 | 12/1997 | Mandeville, III et al. | 514/742 |
| 5,703,188 | 12/1997 | Mandeville, III et al. | 526/290 |

FOREIGN PATENT DOCUMENTS

| | | |
|---|---|---|
| 303 296 A2 | 2/1989 | European Pat. Off. . |
| WO 94 27621 A1 | 12/1994 | WIPO . |
| WO 95 05184 A2 | 2/1995 | WIPO . |
| WO 95 34588 A1 | 12/1995 | WIPO . |
| WO 96 39156 A2 | 12/1996 | WIPO . |
| WO 96 39449 A1 | 12/1996 | WIPO . |
| WO 98 17707 | 4/1998 | WIPO . |

OTHER PUBLICATIONS

Baggio, B. et al., "Correction of Erythrocyte Abnormalities in Idiopathic Calcium–oxalate Nephrolithiasis and Reduction of Urinary Oxalate by Oral Glycosaminoglycans," The Lancet, 338:403–405 (1991).

Drach, G.W. et al., "The Paradox of Inhibition and Enhancement of the Formation of Urinary Stones," Urological Research, 10 (4) :165–168 (1982).

Scurr, D.S. et al., "Polyanionic Inhibitors of Calcium Oxalate Crystal Agglomeration in Urine," Proc. Eur. Dial. Transplant Assoc. 20:440–444 (1983).

Hagmaier, V. et al., "Prüfung der Wirksamkeit eines oxalatbindenden Anionenaustauschers Colestid an gesunden Probanden zum Einsatz bei der idiopathischen Calcium–Oxalat–Urolithiasis", Helvetica Chirurgica Acta, 48: 421–424 (1981). Abstract in English.

Patent Abstracts of Japan, vol. 010, No. 063 (C–332), Mar. 13, 1986 & JP 60 202869 A (Ajinomoto KK), Oct. 14, 1985. Abstract: WPI Acc. No.: 89–048100/198907 (1989).

Hodgkinson, A., Chapter 8. "Human and Animal Pathology." In *Oxalic Acid in Biology and Medicine,* (London: Academic Press) pp. 244–253, (1977).

Lindsjö, M. et al., "Treatment of Enteric Hyperoxaluria with Calcium–Contained Organic Marine Hydrocolloid," The Lancet, Sep. 23, 1989, pp. 701–703.

Smith, L.H., M.D. et al., "Acquired Hyperoxaluria, Nephrolithiasis, and Intestinal Disease," The New England Journal of Medicine, vol. 286, Jun. 29, 1972, No. 26, pp. 1371–1374.

*Primary Examiner*—Kevin E. Weddington
*Attorney, Agent, or Firm*—Hamilton, Brook, Smith & Reynolds, P.C.

[57] ABSTRACT

A method for reducing oxalate levels in a patient that includes administering to the patient a therapeutically effective amount of non-absorbable amine polymers such as a polymer characterized by a repeat unit having the formula:

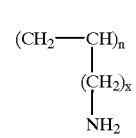

(1)

and salts and copolymers thereof, where n is a positive integer and x is zero or an integer between 1 and about 4.

14 Claims, No Drawings

METHOD FOR REDUCING OXALATE

BACKGROUND OF THE INVENTION

Approximately 0.1% of adults in the USA are hospitalized each year for urinary calculi (e.g. kidney stones), of which about 80% are primarily calcium oxalate. Patients at risk for urinary calculi generally include those with calculi or who have had calculi in the past, those with renal insufficiency, those on diets containing a large amount of oxalate, those with ileal disease, ileal resection, or jejeunoileal bypass, those with chronic biliary or pancreatic disease, and those with a family history of calculi. Thus, there is a need for superior oxalate reducers.

SUMMARY OF THE INVENTION

The invention relates to the discovery that a class of polymers have improved oxalate binding properties. The polymers employed in the invention comprise water-insoluble, non-absorbable, and optionally cross-linked polyamines as defined herein. The polyamines of the invention can be amine or ammonium containing aliphatic polymers. By aliphatic amine polymers, it is meant a polymer which is manufactured by polymerizing an aliphatic amine monomer. In a preferred embodiment, the polymers are characterized by one or more monomeric units of Formula I:

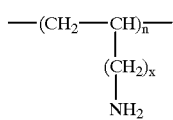

(1)

and salts thereof, where n is a positive integer and x is 0 or an integer between 1 and about 4, preferably 1. In preferred embodiments, the polymer is crosslinked by means of a multifunctional crosslinking agent.

The invention provides an effective treatment for removing oxalate from a patient (and thereby reducing the patient's urinary output of oxalate and urinary calculi). The invention also provides for the use of the polymers described herein for the manufacture of a medicament for the treatment of urinary calculi, for oxalate binding or reduction of oxalate levels.

Other features and advantages will be apparent from the following description of the preferred embodiments thereof and from the claims.

DETAILED DESCRIPTION OF THE INVENTION

As described above, the polymers employed in the invention comprise water-insoluble, non-absorbable, optionally cross-linked polyamines. Preferred polymers are polyallylamine, polyvinylamine and polydiallylamine polymers. The polymers can be homopolymers or copolymers, as discussed below, and can be substituted or unsubstituted. These and other polymers which can be used in the claimed invention have been reported in the patent literature in, for example, U.S. Pat. Nos. 5,487,888, 5,496,545, 5,607,669, 5,618,530, 5,624,963, 5,667,775, 5,679,717, 5,703,188, 5,702,696, and 5,693,675. Copending U.S. application Ser. No. 08/659,264, 08/823699, 08/835,857, 08/470,940, 08/826,197, 08/777,408, 08/927,247, 08/964,498 and 08/964,536, the entire contents of which are incorporated herein by reference.

The polymer can be a homopolymer or a copolymer of one or more amine-containing monomers or a copolymer of one or more amine-containing monomers in combination with one or more non-amine containing monomers. Where copolymers are manufactured with the monomer of the above Formula I, the comonomers are preferably inert, non-toxic and/or possess oxalate binding properties. Examples of suitable non-amine-containing monomers include vinylalcohol, acrylic acid, acrylamide, and vinylformamide. Examples of amine containing monomers preferably include monomers having the Formula 1 above. Preferably, the monomers are aliphatic. Most preferably, the polymer is a homopolymer, such as a homopolyallylamine, homopolyvinylamine or homopolydiallylamine.

Other preferred polymers include polymers characterized by one or more repeat units set forth below

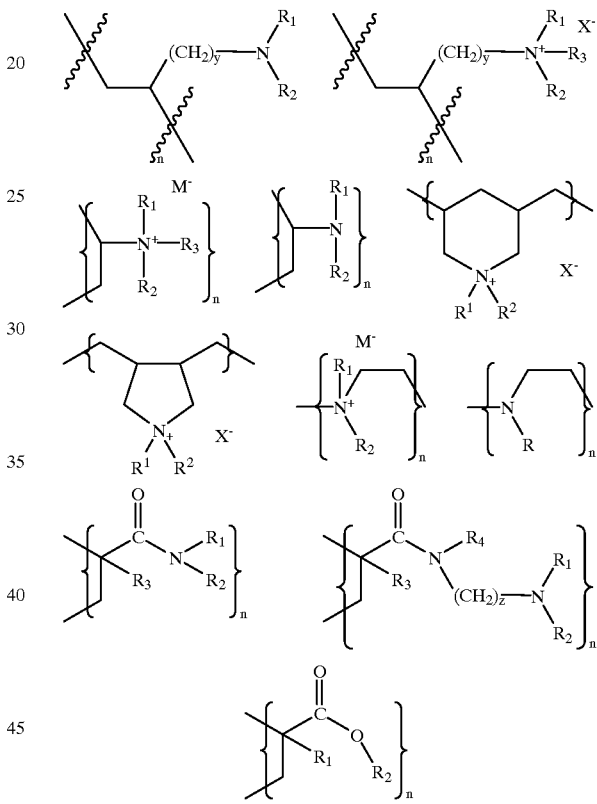

or copolymers thereof, wherein n is a positive integer, y and z are both integers of one or more (e. g. , between about one and about 10) and each R, $R_1$, $R_2$, $R_3$ and $R_4$, independently, is H or a substituted or unsubstituted alkyl group (e. g. , having between 1 and 25 or between 1 and 5 carbon atoms, inclusive), alkylamino (e. g. , having between 1 and 5 carbons atoms, inclusive, such as ethylamino or poly (ethylamino)) or aryl (e.g., phenyl) group, and each X– is an exchangeable negatively charged counterion.

In one preferred polymer, at least one of R, $R_1$, $R_2$, $R_3$ or $R_4$ groups is a hydrogen atom. In a more preferred embodiment, each of these groups are hydrogen.

In each case, the R groups can carry one or more substituents. Suitable substituents include therapeutic anionic groups, e.g., quaternary ammonium groups, or amine groups, e.g., primary, secondary or tertiary alkyl or aryl amines. Examples of other suitable substituents include hydroxy, alkoxy, carboxamide, sulfonamide, halogen, alkyl, aryl, hydrazine, guanadine, urea, poly(alkylenimine), such as (polyethylenimine) and carboxylic acid esters, for example.

Preferably, the polymer is rendered water-insoluble by crosslinking. The cross-linking agent can be characterized by functional groups which react with the amino group of the monomer. Alternatively, the crosslinking group can be characterized by two ore more vinyl groups which undergo free radical polymerization with the amine monomer.

Examples of suitable crosslinking agents include diacrylates and dimethylacrylates (e. g. ethylene glycol diacrylate, propylene glycol diacrylate, butylene glycol diacrylate, ethylene glycol dimethacrylate, propylene glycol dimethacrylate, butylene glycol dimethacrylate, polyethyleneglycol dimethacrylate and polyethyleneglycol diacrylate), methylene bisacrylamide, methylene bismethacrylamide, ethylene bisacrylamide, ethylene bismethacrylamide, ethylidene bisacrylamide, divinylbenzene, bisphenol A, dimethacrylate and bisphenol A diacrylate. The crosslinking agent can also include acryloyl chloride, epichlorohydrin, butanedioldiglycidyl ether, ethanedioldiglycidyl ether, succinyl dichloride, the diglycidal ether of bisphenol A, pyromellitic dianhydride, toluene diisocyanate, ethylene diamine and dimethyl succinate.

A preferred crosslinking agent is epichlorohydrin because of its high availability and low cost. Epichlorohydrin is also advantageous because of its low molecular weight and hydrophilic nature, increasing the water-swellability and gel properties of the polyamine.

The level of crosslinking makes the polymers insoluble and substantially resistant to absorption and degradation, thereby limiting the activity of the polymer to the gastrointestinal tract. Thus, the compositions are non-systemic in their activity and will lead to reduced side-effects in the patient. Typically, the cross-linking agent is present in an amount from about 0.5–35% or about 0.5–25% (such as from about 2.5–20% or about 1–10%) by weight, based upon total weight of monomer plus crosslinking agent.

The polymers can also be further derivatized, such as alkylated amine polymers, as described, for example, in U.S. Pat. Nos. 5,679,717, 5,607,669 and 5,618,530, which are incorporated herein by reference. Preferred alkylating agents include hydrophobic groups (such as aliphatic hydrophobic groups) and/or quaternary ammonium- or amine-substituted alkyl groups.

Non-cross-linked and cross-linked polyallylamine and polyvinylamine are generally known in the art and are commercially available. Methods for the manufacture of polyallylamine and polyvinylamine, and cross-linked derivatives thereof, are described in the above U.S. Patents, the teachings of which are incorporated entirely by reference. Harada et al. (U.S. Pat. Nos. 4,605,701 and 4,528,347, which are incorporated herein by reference in their entirety) also describe methods of manufacturing polyallylamine and cross-linked polyallylamine.

As described above the polymer can be administered in the form of a salt. By "salt" it is meant that the nitrogen group in the repeat unit is protonated to create a positively charged nitrogen atom associated with a negatively charged counterion.

The cationic counterions can be selected to minimize adverse effects on the patient, as is more particularly described below. Examples of suitable counterions include organic ions, inorganic ions, or a combination thereof, such as halides (Cl– and Br–) $CH_3OSO_3^-$, $HSO_4^-$, $SO_4^{2-}$, $HCO_3^-$, $CO_3^-$, acetate, lactate, succinate, propionate, butyrate, ascorbate, citrate, dihydrogen citrate, tartrate, taurocholate, glycocholate, cholate, hydrogen citrate, maleate, benzoate, folate, an amino acid derivative, a nucleotide, a lipid, or a phospholipid. The counterions can be the same as, or different from, each other. For example, the polymer can contain two different types of counterions.

The polymers according to the invention can be administered orally to a patient in a dosage of about 1 mg/kg/day to about 1 g/kg/day, preferably between about 10 mg/kg/day to about 200 mg/kg/day; the particular dosage will depend on the individual patient (e.g., the patient's weight and the extent of oxalate removal required). The polymer can be administrated either in hydrated or dehydrated form, and can be flavored or added to a food or drink, if desired to enhance patient acceptability. Additional ingredients such as other oxalate reducers or binders (including calcium), ingredients for treating other related indications, or inert ingredients, such as artificial coloring agents can be added as well.

For example, an enzyme which can reduce oxalate levels can be coadministered with the polymer. Suitable enzymes include oxalate decarboxylase, oxalate oxidase and additional enzymes that can function collaterally and, for example, convert products of the enzymatic reaction to harmless products. For example, peroxidase can be administered to convert hydrogen peroxide produced by oxalate oxidase.

The additional active ingredients, such as enzymes, can be administered simultaneously or sequentially with the oxalate binding polymer. Where the ingredients are administered simultaneously, the enzyme can optionally be bound to the polymer, for example, by covalent bonding or physically encapsulating the enzyme, on the exterior or interior of the polymeric particle. Covalent bonding can be accomplished by reacting the polymer and enzyme(s) with a suitable crosslinking agent. For example, polyallylamine and an enzyme can be cross-linked with epichlorohydrin, polyacrylamide and an enzyme can be cross-linked with methylenebisacrylamide and poly-2-acrylamido-2-methylpropane sulfonic acid (and its salts) and an enzyme can be cross-linked with methylenebisacrylamide.

Examples of suitable forms for administration (preferably oral administration) include pills, tablets, capsules, and powders (e.g., for sprinkling on food or incorporating into a drink). The pill, tablet, capsule, or powder can be coated with a substance capable of protecting the composition from disintegration in the esophagus but will allow disintegration as the composition in the stomach and mixing with food to pass into the patient's small intestine. The polymer can be administered alone or in combination with a pharmaceutically acceptable carrier substance, e.g., magnesium carbonate, lactose, or a phospholipid with which the polymer can form a micelle.

The polymers of the invention can be used to treat patients, preferably humans, with high urinary or serum oxalate levels or hyperoxaluria or who are at risk of high urinary or serum oxalate levels or hyperoxaluria. For example, patients who can be treated by the administration of the polymers described herein include those who have or have had urinary calculi or kidney stones, those who have renal deficiency due to elevated oxalate levels, those who are on diets containing large amounts of oxalate, those who have ileal disease, ileal resection or jejeunoileal bypass, those who have biliary or pancreatic disease and those with a family history of calculi. Additionally, patients with cardiomyopathy, cardiac conductance disorders, cystic fibrosis, Crohn's disease, renal failure, vulvodynia and depleted colonies of intestinal *Oxalobacter formigenes*.

EXAMPLES

A. Polymer Preparation

1. Poly(vinylamine)

The first step involved the preparation of ethylidenebisacetamide. Acetamide (118 g), acetaldehyde (44.06 g), copper acetate (0.2 g), and water (300 mL) were placed in a 1 L three neck flask fitted with condenser, thermometer, and mechanical stirred. Concentrated HCl (34 mL) was added and the mixture was heated to 45–50° C. with stirring for 24 hours. The water was then removed in vacuo to leave a thick sludge which formed crystals on cooling to 5° C. Acetone (200 mL) was added and stirred for a few minutes, after which the solid was filtered off and discarded. The acetone was cooled to 0° C. and solid was filtered off. This solid was rinsed in 500 mL acetone and air dried 18 hours to yield 31.5 g of ethylidenebis-acetamide.

The next step involved the preparation of vinylacetamide from ethylidenebisacetamide. Ethylidenebisacetamide (31.05 g), calcium carbonate (2 g) and celite 541 (2 g) were placed in a 500 mL three neck flask fitted with a thermometer, a mechanical stirrer, and a distilling head atop a Vigroux column. The mixture was vacuum distilled at 24 mm Hg by heating the pot to 180–225° C. Only a single fraction was collected (10.8 g) which contained a large portion of acetamide in addition to the product (determined by NMR). This solid product was dissolved in isopropanol (30 mL) to form the crude vinylacetamide solution used for polymerization.

Crude vinylacetamide solution (15 mL), divinylbenzene (1 g, technical grade, 55% pure, mixed isomers), and AIBN (0.3 g) were mixed and heated to reflux under a nitrogen atmosphere for 90 minutes, forming a solid precipitate. The solution was cooled, isopropanol (50 mL) was added, and the solid was collected by centrifugation. The solid was rinsed twice in isopropanol, once in water, and dried in a vacuum oven to yield 0.8 g of poly(vinylacetamide), which was used to prepare poly(vinylamine as follows).

Poly(vinylacetamide) (0.79 g) was placed in a 100 mL one neck flask containing water (25 mL) and conc. HCl (25 mL). The mixture was refluxed for 5 days, after which the solid was filtered off, rinsed once in water, twice in isopropanol, and dried in a vacuum oven to yield 0.77 g of product. Infrared spectroscopy indicated that a significant amount of the amide (1656 cm$^{-1}$) remained and that not much amine (1606 cm$^{-1}$) was formed. The product of this reaction (~0.84 g) was suspended in NaOH (46 g) and water (46 g) and heated to boiling (~140° C.). Due to foaming the temperature was reduced and maintained at ~100° C. for 2 hours. Water (100 mL) was added and the solid collected by filtration. After rinsing once in water the solid was suspended in water (500 mL) and adjusted to pH 5 with acetic acid. The solid was again filtered off, rinsed with water, then isopropanol, and dried in a vacuum oven to yield 0.51 g of product. Infrared spectroscopy indicated that significant amine had been formed.

2. Poly(allylamine) hydrochloride

To a 2 liter, water-jacketed reaction kettle equipped with (1) a condenser topped with a nitrogen gas inlet, 92) a thermometer, and (3) a mechanical stirrer was added concentrated hydrochloric acid (360 mL). The acid was cooled to 5° C. using circulating water in the jacket of the reaction kettle (water temperature=0° C.). Allylamine (328.5 mL, 250 g) was added dropwise with stirring while maintaining the reaction temperature at 5–10° C. After addition was complete, the mixture was removed, placed in a 3 liter one-neck flask, and 206 g of liquid was removed by rotary vacuum evaporation at 60° C. Water (20 mL) was then added and the liquid was returned to the reaction kettle. Azobis (amidinopropane) dihydrochloride (0.5 g) was suspended in 11 mL of water was then added. The resulting reaction mixture was heated to 50° C. under a nitrogen atmosphere with stirring for 24 hours. Additional azobis (amidinopropane) dihydrochloride (5 mL) suspended in 11 mL of water was then added, after which heating and stirring were continued for an additional 44 hours.

At the end of this period, distilled water (100 mL) was added to the reaction mixture and the liquid mixture allowed to cool with stirring. The mixture was then removed and placed in a 2 liter separatory funnel, after which it was added dropwise to a stirring solution of methanol (4 L), causing a solid to form. The solid was removed by filtration, re-suspended in methanol (4 L), stirred for 1 hour, and collected by filtration. The methanol rinse was then repeated one more time and the solid dried in a vacuum oven to afford 215.1 g of poly(allylamine) hydrochloride as a granular white solid.

3. Poly(allylamine) Hydrochloride Crosslinked with Epichlorohydrin

To a 5 gallon vessel was added poly(allylamine) hydrochloride prepared as described in Example 2 (1 kg) and water (4 L). The mixture was stirred to dissolve the hydrochloride and the pH was adjusted by adding solid NaOH (284 g). The resulting solution was cooled to room temperature, after which epichlorohydrin crosslinking agent (50 mL) was added all at once with stirring. The resulting mixture was stirred gently until it gelled (about 35 minutes). The crosslinking reaction was allowed to proceed for an additional 18 hours at room temperature, after which the polymer gel was removed and placed in portions in a blender with a total of 10 L of water. Each portion was blended gently for about 3 minutes to form coarse particles which were then stirred for 1 hour and collected by filtration. The solid was rinsed three times by suspending it in water (10 L, 15 L, 20 L), stirring each suspension for 1 hour, and collecting the solid each time by filtration. The resulting solid was then rinsed once by suspending it in isopropanol (17 L), stirring the mixture for 1 hour, and then collecting the solid by filtration, after which the solid was dried in a vacuum oven at 50° C. for 18 hours to yield about 677 g of the cross-linked polymer as a granular, brittle, white solid.

4. Poly(allylamine) Hydrochloride Crosslinked with Butanedioldiglycidyl Ether

To a 5 gallon plastic bucket was added poly(allylamine) hydrochloride prepared as described in Example 2 (500 g) and water (2 L). The mixture was stirred to dissolve the hydrochloride and the pH was adjusted to 10 by adding solid NaOH (134.6 g). The resulting solution was cooled to room temperature in the bucket, after which 1, 4-butanedioldiglycidyl ether crosslinking agent (65 mL) was added all at once with stirring. The resulting mixture was stirred gently until it gelled (about 6 minutes). The crosslinking reaction was allowed to proceed for an additional 18 hours at room temperature, after which the polymer gel was removed and dried in a vacuum oven at 75° C. for 24 hours. The dry solid was then ground and sieved to -30 mesh, after which it was suspended in 6 gallons of water and stirred for 1 hour. The solid was then filtered off and the rinse process repeated two more times. The resulting solid was then air dried for 48 hours, followed by drying in a vacuum oven at 50° C. for 24 hours to yield about 415 g of the crosslinked polymer as a white solid.

5. Poly(allylamine) Hydrochloride Crosslinked with Ethanedioldiglycidyl Ether

To a 100 mL beaker was added poly(allylamine) hydrochloride prepared as described in Example 2 (10 g) and water (40 mL). The mixture was stirred to dissolve the hydrochloride and the pH was adjusted to 10 by adding solid NaOH. The resulting solution was cooled to room temperature in the beaker, after which 1, 2-ethanedioldiglycidyl ether crosslinking agent (2.0 mL) was added all at once with stirring. The resulting mixture was stirred gently until it gelled (about 4 minutes). The crosslinking reaction was allowed to proceed for an additional 18 hours at room temperature, after which the polymer gel was removed and blended in 500 mL of methanol. The solid was then filtered off and suspended in water (500 mL). After stirring for 1 hour, the solid was filtered off and the rinse process repeated. The resulting solid was rinsed twice in isopropanol (400 mL) and then dried in a vacuum oven at 50° C. for 24 hours to yield 8.7 g of the crosslinked polymer as a white solid.

6. Poly(allylamine) Hydrochloride Crosslinked with Dimethylsuccinate

To a 500 mL round bottom flask was added poly (allylamine) hydrochloride prepared as described in Example 2 (10 g), methanol (100 mL), and triethylamine (10 mL). The mixture was stirred and dimethylsuccinate crosslinking agent (1 mL) was added. The solution was heated to reflux and the stirring discontinued after 30 minutes. After 18 hours, the solution was cooled to room temperature, and the solid filtered off and blended in 400 mL of isopropanol. The solid was then filtered off and suspended in water (1 L). After stirring for 1 hour, the solid was filtered off and the rinse process repeated two more times. The solid was then rinsed once in isopropanol (800 mL) and dried in a vacuum oven at 50° C. for 24 hours to yield 5.9 g of the crosslinked polymer as a white solid.

7. Poly(allyltrimethylammonium Chloride)

To a 500 mL three necked flask equipped with a magnetic stirrer, a thermometer, and a condenser topped with a nitrogen inlet, was added poly(allylamine) crosslinked with epichlorohydrin (5.0 g), methanol (300 mL), methyl iodide (20 mL), and sodium carbonate (50 g). The mixture was then cooled and water was added to total volume of 2 L. Concentrated hydrochloric acid was added until no further bubbling resulted and the remaining solid was filtered off. The solid was rinsed twice in 10% aqueous NaCl (1 L) by stirring for 1 hour followed by filtration to recover the solid. The solid was then rinsed three times by suspending it in water (2 L), stirring for 1 hour, and filtering to recover the solid. Finally, the solid was rinsed as above in methanol and dried in a vacuum over at 50° C. for 18 hours to yield 7.7 g of white granular solid.

8. Poly(ethyleneimine)/Acryloyl Chloride

Into a 5 L three neck flask equipped with a mechanical stirrer, a thermometer, and an additional funnel was added polyethyleneimine (510 g of a 50% aqueous solution (equivalent to 255 g of dry polymer) and isopropanol (2.5 L). Acryloyl chloride (50 g) was added dropwise through the addition funnel over a 35 minute period, keeping the temperature below 29° C. The solution was then heated to 60° C. with stirring for 18 hours. The solution was cooled and solid immediately filtered off. The solid was rinsed three times by suspending it in water (2 gallons), stirring for 1 hour, and filtering to recover the solid. The solid was rinsed once by suspending it in methanol (2 gallons), stirring for 30 minutes, and filtering to recover the solid. Finally, the solid was rinsed as above in isopropanol and dried in a vacuum over at 50° C. for 18 hours to yield 206 g of light orange granular solid.

9. Poly(dimethylaminopropylacrylamide)

Dimethylamino-propylacrylamide (10 g) and methylenebisacrylamide (1.1 g) were dissolved in 50 mL of water in a 100 mL three neck flask. The solution was stirred under nitrogen for 10 minutes. Potassium persulfate (0.3 g) and sodium metabisulfite (0.3 g) were each dissolved in 2–3 mL of water and then mixed. After a few seconds this solution was added to the monomer solution, still under nitrogen. A gel formed immediately and was allowed to sit overnight. The gel was removed and blended with 500 mL of isopropanol. The solid was filtered off and rinsed three times with acetone. The solid white powder was filtered off and dried in a vacuum oven to yield 6.1 g.

10. Poly(Methacrylamidopropyltrimethylammoniumchloride)=[Poly (MAPTAC)]

[3-(Methacryloylamino)propyl]trimethylammonium chloride (38 mL of 50% aqueous solution) and methylenebis-methacrylamide (2.2 g) were stirred in a beaker at room temperature. Methanol (10 mL was added and the solution was warmed to 40° C. to fully dissolve the bisacrylamide. Potassium persulfate (0.4 g) was added and the solution stirred for 2 minutes. Potassium metabisulfite (0.4 g) was added and stirring was continued. After 5 minutes the solution was put under a nitrogen atmosphere. After 20 minutes the solution contained significant precipitate and the solution was allowed to sit overnight. The solid was washed three times with isopropanol and collected by filtration. The solid was then suspended in water 500 (mL) and stirred for several hours before being collected by centrifugation. The solid was again washed with water and collected by filtration. The solid was then dried in a vacuum oven to yield 21.96 g.

11. Poly(ethyleneimine) "A"

Polyethyleneimine (50 g of a 50% aqueous solution; Scientific Polymer Products) was dissolved in water (100 mL). Epichlorohydrin (4.6 mL) was added dropwise. The solution was heated to 55° C. for 4 hours, after which it had gelled. The gel was removed, blended with water (1 L) and the solid was filtered off. It was resuspended in water (2 L) and stirred for 10 minutes. The solid was filtered off, the rinse repeated once with water and twice with isopropanol, and the resulting gel was dried in a vacuum oven to yield 26.3 g of a rubbery solid.

Poly(ethyleneimine) "B" and Poly(ethyleneimine) "C" were made in a similar manner, except using 9.2 and 2.3 mL of epichlorohydrin, respectively.

12. Poly(methylmethacrylate-co-divinylbenzene)

Methylmethacrylate (50 g) and divinylbenzene (5 g) and azobisiso-butyronitrile (1.0 g) were dissolved in isopropanol (500 mL) and heated to reflux for 18 hours under a nitrogen 14 atmosphere. The solid white precipitate was filtered off, rinsed once in acetone (collected by centrifugation), once in water (collected by filtration) and dried in a vacuum oven to yield 19.4 g.

13. Poly(diethylenetriaminemethacrylamide)

Poly(methyl-methacrylate-co-divinylbenzene) (20 g) was suspended in diethylenetriamine (200 mL) and heated to reflux under a nitrogen atmosphere for 18 hours. The solid was collected by filtration, resuspended in water (500 mL), stirred 30 minutes, filtered off, resuspended in water (500 mL), stirred 30 minutes, filtered off, rinsed briefly in isopropanol, and dried in a vacuum oven to yield 18.0 g.

Poly(pentaethylenehexaminemethacrylamide), Poly(tetraethylenepentaminemethacrylamide), and Poly(triethylenetetraaminemethacrylamide) were made in a manner similar to poly(diethylenetriaminemethacrylamide) from pentaethylenehexamine, tetraethylenepentamine, and triethylenetetraamine, respectively.

14. Poly(methylmethacrylate/PEI)

Poly(methylmethacrylate-co-divinylbenzene) (1.0 g) was added to a mixture containing hexanol (9150 mL) and polyethyleneimine (15 g in 15 g water). The mixture was heated to reflux under nitrogen for 4 days. The reaction was cooled and the solid was filtered off, suspended in methanol (300 mL), stirred 1 hour, and filtered off. The rinse was repeated once with isopropanol and the solid was dried in a vacuum oven to yield 0.71 g.

15. Poly(aminoethylmethacrylamide)

Poly(methylmethacrylate-co-divinylbenzene) (20 g) was suspended in ethylenediamine 9200 mL) and heated to reflux under a nitrogen atmosphere for 3 days. The solid was collected by centrifugation, washed by resuspending it in water (500 mL), stirring for 30 minutes, and filtering off the solid. The solid was washed twice more in water, once in isopropanol, and dried in a vacuum oven to yield 17.3 g.

16. Poly(diethylaminopropylmethacrylamide)

Poly(methyl-methacrylate-co-divinylbenzene) (20 g) was suspended in diethylaminopropylamine (200 mL) and heated to reflux under a nitrogen atmosphere for 18 hours. The solid was collected by filtration, resuspended in water (500 mL), filtered off, resuspended in water (500 mL), collected by filtration, rinsed briefly in isopropanol, and dried in a vacuum oven to yield 8.2 g.

17. NHS-acrylate

N-Hydroxysuccinimide (NHS, 157.5 g) was dissolved in chloroform (2300 mL) in a 5 L flask. The solution was cooled to 0° C. and acryloyl chloride (132 g) was added dropwise, keeping the temperature 20° C. After addition was complete, the solution was stirred for 1.5 hours, rinsed with water (1100 mL) in a separatory funnel and dried over anhydrous sodium sulfate. The solvent was removed under vacuum and a small amount of ethyl acetate was added to the residue. This mixture was poured into hexane (200 mL) with stirring. The solution was heated to reflux, adding more ethyl acetate (400 mL). The insoluble NHS was filtered off, hexane (1 L) was added, the solution was heated to reflux, ethyl acetate (400 mL) was added, and the solution allowed to cool to <10° C. The solid was then filtered off and dried in a vacuum oven to yield 125.9 g. A second crop of 80 g was subsequently collected by further cooling.

18. Poly (NHS-acrylate)

NHS-acrylate (28.5 g), methylenebis-acrylamide (1.5 g) and tetrahydrofuran (500 mL) were mixed in a 1 L flask and heated to 50° C. under a nitrogen atmosphere. Azobisisobutyronitrile (0.2 g) was added, the solution was stirred for 1 hour, filtered to remove excess N-hydroxyvsuccinimide, and heated to 50° C. for 4.5 hours under a nitrogen atmosphere. The solution was then cooled and the solid was filtered off, rinsed in tetrahydrofuran, and dried in a vacuum oven to yield 16.1 g.

19. Poly(guanidinobutylacrylamide)

Poly(NHS-acrylate) (1 5 g) was suspended in water (25 mL) containing agmatine (1.5 g) which had been adjusted to pH 9 with solid NaOH. The solution was stirred for 4 days, after which time the pH had dropped to 6.3. Water was added to a total of 500 mL, the solution was stirred for 30 minutes and the solid was filtered off. The solid was rinsed twice in water, twice in isopropanol, and dried in a vacuum oven to yield 0.45 g.

20. Poly(methacryloyl chloride)

Methacryloyl chloride (20 mL), divinyl benzene (4 mL of 80% purity), AIBN (0.4 g), and THF (150 mL) were stirred at 60° C. under a nitrogen atmosphere for 18 hours. The solution was cooled and the solid was filtered off, rinsed in THF, then acetone, and dried in a vacuum oven to yield 8.1 g.

21. Poly (guanidinobutylmethacrylamide) Poly (methacryloyl chloride) (0.5 g), agmatine sulfate (1.0 g), triethylamine (2.5 mL), and acetone (50 mL) were stirred together for 4 days. Water (100 mL) was added and the mixture stirred for 6 hours. The solid was filtered off and washed by resuspending in water (500 mL), stirring for 30 minutes, and filtering off the solid. The wash was repeated twice in water, once in methanol, and the solid was dried in a vacuum oven to yield 0.41 g.

22. Poly(guanidinoacrylamide)

The procedure for poly-(guanidinobutylacrylamide) was followed substituting aminoguanidine bicarbonate (5.0 g) for the agmatine, yielding 0.75 g.

23. Poly(PEH/EPI)

Epichlorohydrin (1.5 g) was added dropwise to a solution containing pentaethylenehexamine (PEH) (20 g) and water (100 mL), keeping the temperature between 65° C. The solution was stirred until it gelled and heating was continued for 4 hours (at 65° C.). After sitting overnight at room temperature the gel was removed and blended with water (1 L). The solid was filtered off, water was added (1 L), and the blending and filtration were repeated. The gel was suspended in isopropanol and the resulting solid was collected by filtration and dried in a vacuum oven to yield 28.2 g.

24. Ethylidenebisacetamide

Acetamide (118 g), acetaldehyde (44.06 g), copper acetate (0.2 g), and water (300 mL) were placed in a 1 L three neck flask fitted with condenser, thermometer, and mechanical stirred. Concentrated HCl (34 mL) was added and the mixture was heated to 45–50° C. with stirring for 24 hours. The water was then removed in vacuo to leave a thick sludge which formed crystals on cooling to 5° C. Acetone (200 mL) was added and stirred for a few minutes after which the solid was filtered off and discarded. The acetone was cooled to 0° C. and solid was filtered off. This solid was rinsed in 500 mL acetone and air dried 18 hours to yield 31.5 g.

25. Vinylacetamide

Ethylidenebisacetamide (31.05), calcium carbonate (2 g) and celite 541 (2 g) were placed in a 500 mL three neck flask fitted with a thermometer, a mechanical stirrer, and a distilling head atop a vigroux column. The mixture was vacuum distilled at 35 mm Hg by heating the pot to 180–225° C. Only a single fraction was collected (10. 8 g) which contained a large portion of acetamide in addition to the product (determined by NMR). This solid product was dissolved in isopropanol (30 mL) to form the crude solution used for polymerization.

26. Poly(vinylacetamide)

Crude vinylacetamide solution (15 mL), divinylbenzene (1 g, technical grade, 55% pure, mixed isomers), and AIBN (0. 3 g) were mixed and heated to reflux under a nitrogen atmosphere for 90 minutes, forming a solid precipitate. The solution was cooled, isopropanol (50 mL) was added, and the solid was collected by centrifugation. The solid was rinsed twice in isopropanol, once in water, and dried in a vacuum oven to yield 0.8 g.

27. Poly(vinylamine) Poly(vinylacetamide) (0.79 g) was placed in a 100 mL one neck flask containing water 25 mL and concentrated HCl 25 mL. The mixture was refluxed for 5 days, the solid was filtered off, rinsed once in water, twice in isopropanol, and dried in a vacuum oven to yield 0.77 g. The product of this reaction (~0.84 g) was suspended in NaOH (46 g) and water (46 g) and heated to boiling (~140° C.). Due to foaming the temperature was reduced and maintained at ~100° C. for 2 hours. Water (100 mL) was added and the solid collected by filtration. After rinsing once in water the solid was suspended in water (500 mL) and adjusted to pH 5 with acetic acid. The solid was again filtered off, rinsed with water, then the isopropanol, and dried in a vacuum oven to yield 0.51 g.

28. Poly(ethyleneimine) Salts

Polyethyleneimine (25 g dissolved in 25 g water) was dissolved in water (100 mL) and mixed with toluene (1 L). Epichlorohydrin (2.3 mL) was added and the mixture heated to 60° C. with vigorous mechanical stirring for 18 hours. The mixture was cooled and the solid filtered off, resuspended in methanol (2 L), stirred 1 hour, and collected by centrifugation. The solid was suspended in water (2 L), stirred 1 hour, filtered off, suspended in water (4 L), stirred 1 hour, and again filtered off. The solid was suspended in acetone (4 L) and stirred 15 minutes, the liquid was poured off, acetone (2 L) was added, the mixture was stirred 15 minutes, the acetone was again poured off, and the solid was dried in a vacuum oven to form intermediate "D".

29. Poly(ethyleneimine sulfate A)

Intermediate "D" (1.0 g) was suspended in water (150 mL), stirred 30 minutes, and partially neutralized with sulfuric acid (1.1 g). The mixture was stirred an additional 30 minutes, the solid was filtered off, resuspended in methanol (200 mL), stirred 5 minutes, filtered off, and dried in a vacuum oven.

30. Poly(ethyleneimine sulfate B)

Intermediate "D" (1.0 g) was suspended in water (150 mL), stirred 30 minutes, and partially neutralized with sulfuric acid (0.57 g). The mixture was stirred an additional 30 minutes, the solid was filtered off, resuspended in methanol (200 mL), stirred 5 minutes, filtered off, and dried in a vacuum oven.

31. Poly(ethyleneimine sulfate C)

Intermediate "D" (1.0 g) was suspended in water (150 mL), stirred 30 minutes, and partially neutralized with sulfuric acid (0.28 g). The mixture was stirred an additional 30 minutes, the solid was filtered off, resuspended in methanol (200 mL), stirred 5 minutes, filtered off, and dried in a vacuum oven.

32. Poly(ethyleneimine sulfate D)

Intermediate "D" (1. 0 g) was suspended in water (150 mL), stirred 30 minutes, and partially neutralized with sulfuric acid (0.11 g). The mixture was stirred an additional 30 minutes, the solid was filtered off, resuspended in methanol (200 mL), stirred 5 minutes, filtered off, and dried in a vacuum oven.

33. Poly(ethyleneimine tartrate A)

Intermediate "D" (1. 0 g) was suspended in water (150 mL), stirred 30 minutes, and partially neutralized with tartaric acid (1.72 g). The mixture was stirred an additional 30 minutes, the solid was filtered off, resuspended in methanol (200 mL), stirred 5 minutes, filtered off, and dried in a vacuum oven.

34. Poly(ethyleneimine tartrate B)

Intermediate "D" (1.0 g) was suspended in water (150 mL), stirred 30 minutes, and partially neutralized with tartaric acid (0.86 g). The mixture was stirred an additional 30 minutes, the solid was filtered off, resuspended in methanol (200 mL), stirred 5 minutes, filtered off, and dried in a vacuum oven.

35. Poly(ethyleneimine tartrate C)

Intermediate "D" (1.0 g) was suspended in water (150 mL), stirred 30 minutes, and partially neutralized with tartaric acid (0.43 g). The mixture was stirred an additional 30 minutes, the solid was filtered off, resuspended in methanol (200 mL), stirred 5 minutes, filtered off, and dried in a vacuum oven.

36. Poly(ethyleneimine ascorbate A)

Intermediate "D" (1.0 g) was suspended in water (150 mL), stirred 30 minutes, and partially neutralized with ascorbic acid (4.05 g). The mixture was stirred an additional 30 minutes, the solid was filtered off, resuspended in methanol (200 mL), stirred 5 minutes, filtered off, and dried in a vacuum oven.

37. Poly(ethyleneimine ascorbate P)

Intermediate "D" (1.0 g) was suspended in water (150 mL), stirred 30 minutes, and partially neutralized with ascorbic acid (2.02 g). The mixture was stirred an additional 30 minutes, the solid was filtered off, resuspended in methanol (200 mL), stirred 5 minutes, filtered off, and dried in a vacuum oven.

38. Poly(ethyleneimine ascorbate C)

Intermediate "D" (1. 0 g) was suspended in water (150 mL), stirred 30 minutes, and partially neutralized with ascorbic acid (1.01 g). The mixture was stirred an additional 30 minutes, the solid was filtered off, resuspended in methanol (200 mL), stirred 5 minutes, filtered off, and dried in a vacuum oven.

39. Poly(ethyleneimine citrate A)

Intermediate "D" (1. 0 g) was suspended in water (150 mL), stirred 30 minutes, and partially neutralized with citric acid (1.47 g). The mixture was stirred an additional 30 minutes, the solid was filtered off, resuspended in methanol (200 mL), stirred 5 minutes, filtered off, and dried in a vacuum oven.

40. Poly(ethyleneimine citrate B)

Intermediate "D" (1.0 g) was suspended in water (150 mL), stirred 30 minutes, and partially neutralized with citric acid (0.74 g). The mixture was stirred an additional 30 minutes, the solid was filtered off, resuspended in methanol (200 mL), stirred 5 minutes, filtered off, and dried in a vacuum oven.

41. Poly(ethyleneimine citrate C)

Intermediate "D" (1.0 g) was suspended in water (150 mL), stirred 30 minutes, and partially neutralized with citric acid (0.37 g). The mixture was stirred an additional 30 minutes, the solid was filtered off, resuspended in methanol (200 mL), stirred 5 minutes, filtered off, and dried in a vacuum oven.

42. Poly(ethyleneimine succinate A)

Intermediate "D" (1.0 g) was suspended in water (150 mL), stirred 30 minutes, and partially neutralized with succinic acid (1.36 g). The mixture was stirred an additional 30 minutes, the solid was filtered off, resuspended in methanol (200 mL), stirred 5 minutes, filtered off, and dried in a vacuum oven.

43. Poly(ethyleneimine succinate B)

Intermediate "ID" (1.0 g) was suspended in water (150 mL), stirred 30 minutes, and partially neutralized with succinic acid (0.68 g). The mixture was stirred an additional 30 minutes, the solid was filtered off, resuspended in methanol (200 mL), stirred 5 minutes, filtered off, and dried in a vacuum oven.

44. Poly(ethyleneimine chloride)

Polyethyleneimine (100 g in 100 g water) was dissolved in water (640 mL additional) and the pH was adjusted to 10 with concentrated HCl. Isopropanol (1.6 L) was added, followed by epichlorohydrin (19.2 mL). The mixture was stirred under nitrogen for 18 hours at 60° C. The solids were filtered off and rinsed with methanol (300 mL) on the funnel. The solid was rinsed by resuspending it in methanol (4 L), stirring 30 minutes, and filtering off the solid. The rinse was repeated twice with methanol, followed by resuspension in water (1 gallon). The pH was adjusted to 1.0 with concentrated HCl, the solid was filtered off, resuspended in water (1 gallon), the pH again adjusted to 1.0 with concentrated HCl, the mixture stirred 30 minutes, and the solid filtered off. The methanol rinse was again repeated and the solid dried in a vacuum oven to yield 112.4 g.

45. Poly(dimethylethyleneimine chloride)

Poly(ethyleneimine chloride) (5.0 g) was suspended in methanol (300 mL) and sodium carbonate (50 g) was added. Methyl iodide (20 mL) was added and the mixture heated to reflux for 3 days. Water was added to reach a total volume of 500 mL, the mixture stirred for 15 minutes, and the solid filtered off. The solid was suspended in water (500 mL), stirred 30 minutes, and filtered. The solid was suspended in water (1 L), the pH adjusted to 7.0 with concentrated HCl, and the mixture stirred for 10 minutes. The solid was filtered off, resuspended in isopropanol (1 L), stirred 30 minutes, filtered off, and dried in a vacuum oven to yield 6.33 g.

46. Poly(methacryloyl chloride)

Methacryloyl chloride (20 mL), divinyl benzene (4 mL of 80% purity), AIBN (0.4 g), and THF (150 mL) were stirred at 60° C. under a nitrogen atmosphere for 18 hours. The solution was cooled, and the solid was filtered off, rinsed in THF, then acetone, and dried in a vacuum oven to yield 8.1 g.

47. Poly(guanidinobutylmethacrylamide)

Poly(methacryloyl chloride) (0.5 g), agmatine sulfate (1.0 g), triethylamine (2.5 mL), and acetone (50 mL) were stirred together for 4 days. Water (100 mL) was added, and the mixture stirred for 6 hours. The solid was filtered off, washed by resuspending in water (500 mL), stirring for 30 minutes, and filtering off the solid. The wash was repeated twice in water, once in methanol, and the solid was dried in a vacuum oven to yield 0.41 g.

48. Poly(PEH/EPI)

Epichlorohydrin (21.5 g) was added dropwise to a solution containing pentaethylenehexamine (20 g) and water (100 mL), keeping the temperature below 65° C. The solution was stirred until it gelled, and heating was continued for 4 hours (at 65° C.). After sitting overnight at room temperature, the gel was removed and blended with water (1 L). The solid was filtered off, water was added (1 L), and the blending and filtration were repeated. The gel was suspended in isopropanol, and the resulting solid was collected by filtration and dried in a vacuum oven to yield 28.2 g.

49. Poly(TAEA-acrylamide)

Poly(NHS-acrylate) (4.4 g) was suspended in a solution containing water (100 mL) and tris(2-aminoethyl)amine (30 mL) which had been adjusted to pH 9 with concentrated HCl. After 4 days of stirring, the solid was filtered off, and the wash repeated. The solid was then rinsed briefly with water twice, isopropanol once, and dried in a vacuum oven to yield 3.4 g.

50. Poly(PEH-acrylamide)

Poly(NHS-acrylate) (5.0 g) was suspended in a solution containing water (100 mL) and pentaethylene hexamine (30 mL) which had been adjusted to pH 10 with concentrated HCl. After 4 days of stirring, the solid was filtered off and resuspended in water (500 mL). The mixture was stirred for 4 hours, the solid was filtered off, and the wash repeated. The solid was then rinsed briefly with water twice, isopropanol once, and dried in a vacuum oven to yield 4.7 g.

51. Poly(MI/EPI)

To a 500 mL flask was added 2-methylimidazole (41.00 g, 0.50 mol) and water (100 mL). The solution was heated to 55° C., and epichlorohydrin (46.3 g. 0.50 mol) was added dropwise over 100 minutes. The maximum temperature reached during the addition was 75° C. When the addition was complete, the solution was heated to 90° C. and held at that temperature for 18 hours. In the morning, the reaction was cooled to 45° C., and epichlorohydrin (8.7 g, 0.094 mol) was added dropwise. After the addition was complete, the solution was stirred at 45° C. for 2 hours. At this point, a solution of sodium hydroxide (3.78 g, 0.094 mol) in water (15 mL) was prepared. The reaction was cooled, and the sodium hydroxide solution was added dropwise at 28° C. over 10 minutes. The solution was stirred for an additional 15 minutes and then transferred to a beaker and heated to 95° C. on a hot plate. When the reaction solidified, it was placed in an oven at 125° C. for 5 hours to cure. After cooling to room temperature, the polymer was broken up and added to 2000 mL of water. The mixture was allowed to stand for 3 hours and then blended in two portions. The hydrated gel was filtered and then dehydrated with isopropanol in two steps in the blender. Filtration and vacuum drying afforded 83.51 g of title polymer.

52. Poly(2-acrylamido-2-methyl propane sulfonic acid) (10% crosslinking) containing Oxalate Decarboxylase To a 10 mL beaker was added 2-acrylamido-2-methylpropane sulfonic acid (0.25 g) water (2.5 mL), methylenebisacrylamide (0.028 g), and oxalate decarboxylase (3 mg; from C. Velutipes; Sigma). Nitrogen gas was bubbled through the sample for 10 minutes, followed by the addition of potassium persulfate (3 mg) and potassium metabisulfite (3 mg). The mixture was allowed to sit for 18 hours and was broken up in a blender in aqueous sodium citrate (500 mL; 0.2 M). The solid was collected by filtration and tested as is.

53. Poly(2-acrylamido-2-methyl propane sulfonic acid) (5% crosslinking) containing Oxalate Decarboxylase To a 10 mL beaker was added 2-acrylamido-2-methylpropane sulfone acid (0. 25 g) water (2. 5 mL), methylenebisacrylamide (0. 014 g), and oxalate decarboxylase (3 mg; from C. Velutipes; Sigma). Nitrogen gas was bubbled through the sample for 10 minutes, followed by the addition of potassium persulfate (3 mg) and potassium metabisulfite (3 mg). The mixture was allowed to sit for 18 hours, followed by a second addition of potassium persulfate (3 mg) and potassium metabisulfite (3 mg). After an additional 18 hours, the gel was broken up in a blender in aqueous sodium citrate (500 mL; 0.2 M; pH 4). The solid was collected by filtration and tested as is.

54. Copoly(Acrylamide-co-2-acrylamido-2-methyl propane sulfonic acid) (10% crosslinking) containing Oxalate Decarboxylase To a 10 mL beaker was added 2-acrylamido-2-methylpropane sulfonic acid (0.186 g), acrylamide (0.064 g), water 2.5 mL), methylenebisacrylamide (0.028 g), and oxalate decarboxylase (3 mg; from C. Velutipes; Sigma). Nitrogen gas was bubbled through the sample for 10 minutes, followed by the addition of potassium persulfate (6 mg) and potassium metabisulfite (6 mg). The mixture was allowed to sit for 18 hours and was broken up in a blender in aqueous sodium citrate (500 mL; 0.2 M; pH 4). The solid was collected by filtration and tested as is.

55. Poly(Acrylamide) containing Oxalate Decarboxylase

To a 10 mL beaker was added acrylamide (0.25 g), water (2.5 mL), methylenebisacrylamide (0.027 g), and oxalate decarboxylase (3 mg; from C. Velutipes; Sigma). Nitrogen gas was bubbled through the sample for 10 minutes, followed by the addition of potassium persulfate (6 mg) and potassium metabisulfite (6 mg). The mixture was allowed to sit for 18 hours and was broken up in a blender in aqueous sodium citrate (500 mL; 0.2 M; pH 4). The solid was collected by filtration and tested as is.

56. Polyallylamine Crosslinked with Epichlorohydrin

An aqueous solution of poly(allylamine hydrochloride) (500 lb of a 50.7% aqueous solution) was diluted with water (751 lb) and neutralized with aqueous sodium hydroxide (171 lb of a 50% aqueous solution). The solution was cooled to approximately 25° C., and acetonitrile (1340 lb) and epichlorohydrin (26.2 lb) were added. The solution was stirred vigorously for 21 hours. During this time, the reactor contents changed from two liquid phases to a slurry of particles in a liquid. The solid gel product was isolated by filtration. The gel was washed in an elutriation process with water (136,708 lb). The gel was isolated by filtration and rinsed with isopropanol. The gel was slurried with isopropanol (1269 lb) and isolated by filtration. The isopropanol/water wet gel was dried in a vacuum dryer at 60° C. The dried product was ground to pass through a 50 mesh screen to give a product suitable for pharmacologic use (166 lb, 73%).

In Vitro Testing

Some embodiments were tested by stirring them in an oxalate-containing solution at pH 7, typically for 3 hours. The solution was designed to mimic the conditions present in the small intestine. Most tests were run using 1 mM oxalate solution, but some tests used higher concentrations. The table below shows the exact test solution.

| Solution Contents |
| --- |
| 1 mM Oxalic Acid |
| 80 mM Sodium Chloride |
| 30 mM Sodium Carbonate |
| Adjusted to pH 7 with concentrated HCl |

The pH was adjusted to pH 7, once at the start of the test and again at the end of the test, using either 1 M NaOH or 1 M HCl. After 3 hours (unless otherwise indicated), the polymer was filtered, and the residual oxalate concentration in the test solution was determined spectrophotometrically. The difference between the initial oxalate concentration and the final concentration was used to determine the amount of oxalate bound to, or destroyed by, the polymer. This result is expressed in milliequivalents per gram of starting polymer (meq/g).

The table below shows the results obtained for several examples. Higher numbers indicate a more effective polymer.

| Polymer | Oxalate Bound (meq/g)* |
| --- | --- |
| Polyethyleneimine "A" | 0.24 |
| Polyethyleneimine "B" | 0.09 |
| Poly(MI/EPI) | 0.08 |
| Poly(dimethylaminopropylacrylamide) | 0.08 |
| Poly(PEH/EP) | 0.07 |
| Poly(diethylenetriaminemethacrylamide) | 0.04 |
| Poly(MAPTAC) | 0.04 |
| Poly(PEH-acrylamide) | 0.02 |
| Poly(aminopropylacrylamide) HCl | 0.01 |
| Poly(TAEA-acrylamide) | 0.01 |
| Poly(guanidinobutylmethacrylamide) | 0.01 |

*The values apply when the residual solution oxalate levels are ~0.5 to 0.8 mM.

For comparison purposes, the table below shows results obtained in similar tests using other oxalate-binding materials. By comparison to the known oxalate binders shown below, the polymers of the present invention are potent oxalate binding agents.

| Polymer | Oxalate Bound (meq/g)* |
| --- | --- |
| Calcium Lactate | 1.8 |
| Ox-Absorb ® | 0.09 |
| Aluminum Hydroxide, Dried Gel | 0.04 |

*The values apply when the residual solution oxalate levels are ~0.5 to 0.9 mM.

Oxalate binding was also tested at concentrations other than those in the previous examples. The polymers of the present invention bind more oxalate as the oxalate concentration rises.

Polymers of the present invention that contain oxalate degrading enzymes (e.g., oxalate decarboxylase) can also be tested in a similar manner. The table below shows the effectiveness of several of these materials. From the amount of oxalate destroyed per gram of dry equivalent polymer, these materials are potent oxalate eliminating agents.

| Polymer | Enzyme | pH | Oxalate Destroyed (meq/g)* |
| --- | --- | --- | --- |
| Acrylamide | Oxalate Decarboxylase | 3 | 1.5 |
| 10% x-link | Oxalate Decarboxylase | 5 | 0.3 |
|  | Oxalate Decarboxylase | 7 | — |
| AMPS | Oxalate Decarboxylase | 3 | 0.6 |
| 5% x-link | Oxalate Decarboxylase | 5 | 0.5 |
|  | Oxalate Decarboxylase | 7 | 0.5 |
| AMPS | Oxalate Decarboxylase | 3 | 0.6 |
| 10% x-link | Oxalate Decarboxylase | 5 | 1.0 |
|  | Oxalate Decarboxylase | 7 | — |
| AMPS/Acrylamide | Oxalate Decarboxylase | 3 | 0.40 |
| 10% x-link | Oxalate Decarboxylase | 5 | .3 |
|  | Oxalate Decarboxylase | 7 | — |

*The values apply when the residual solution oxalate levels are ~10 mM. Values are meq/g of dry polymer equivalent.

It should be understood, however, that the foregoing description of the invention is intended merely to be illustrative by way of example only and that other modifications, embodiments, and equivalents may be apparent to those skilled in the art without departing from its spirit.

What is claimed is:

1. A method for reducing oxalate levels in a patient in need thereof comprising administering to said patient a therapeutically effective amount of one or more crosslinked homopolymer polymers characterized by a repeat unit having the formula:

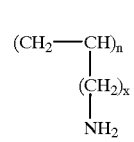

(1)

and salts, where n is a positive integer and x is zero or an integer between 1 and about 4.

2. The method of claim 1 wherein said polymer is crosslinked by means of a multifunctional crosslinking agent, said agent being present in an amount from about 0.5–25% by weight, based upon the combined weight of monomer and crosslinking agent.

3. The method of claim 2 wherein said crosslinking agent is present in an amount from about 2.5–20% by weight, based upon the combined weight of monomer and crosslinking agent.

4. The method of claim 2 wherein said crosslinking agent comprises epichlorohydrin.

5. The method of claim 1, wherein x is 1.

6. The method of claim 1 wherein x is 0.

7. A method of reducing oxalate levels in a patient comprising administering to said patient a therapeutically effective amount of cross-linked homopolyallylamine.

8. The method of claim 7 wherein said cross-linked homopolyallylamine is crosslinked by means of a multifunctional crosslinking agent, said agent being present in an amount from about 1–25% by weight, based upon the combined weight of monomer and crosslinking agent.

9. The method of claim 8, wherein said crosslinking agent is present in an amount from about 2.5–20% by weight, based upon the combined weight of monomer and crosslinking agent.

10. The method of claim 9 wherein said crosslinking agent comprises epichlorohydrin.

11. A method of reducing oxalate levels in a patient comprising administering to said patient a therapeutically effective amount of cross-linked homopolyvinylamine.

12. The method of claim 11, wherein said cross-linked homopolyvinylamine is crosslinked by means of a multifunctional crosslinking agent, said agent being present in an amount from about 1–25% by weight, based upon the combined weight of monomer and crosslinking agent.

13. The method of claim 12 wherein said crosslinking agent is present in an amount from about 2.5–20% by weight, based upon the combined weight of monomer and crosslinking agent.

14. The method of claim 13 wherein said crosslinking agent comprises epichlorohydrin.

* * * * *